(12) United States Patent
Dillon

(10) Patent No.: US 7,879,049 B2
(45) Date of Patent: Feb. 1, 2011

(54) DEVICE TO OPEN AND CLOSE A BODILY WALL

(75) Inventor: Travis E. Dillon, Winston-Salem, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 350 days.

(21) Appl. No.: 12/191,285

(22) Filed: Aug. 13, 2008

(65) Prior Publication Data

US 2009/0054895 A1    Feb. 26, 2009

Related U.S. Application Data

(60) Provisional application No. 60/956,569, filed on Aug. 17, 2007.

(51) Int. Cl.
  *A61B 17/04* (2006.01)
  *A61B 18/14* (2006.01)
(52) U.S. Cl. ............... 606/144; 606/45; 606/139
(58) Field of Classification Search ........... 606/41, 606/45, 139, 144–150; 623/23.72
  See application file for complete search history.

(56) References Cited

U.S. PATENT DOCUMENTS

| | | |
|---|---|---|
| 1,037,864 A | 9/1912 | Carlson |
| 2,880,728 A | 4/1959 | Rights |
| 3,470,875 A | 10/1969 | Johnson |
| 3,513,848 A | 5/1970 | Winston et al. |
| 3,809,081 A | 5/1974 | Loveless |
| 4,236,470 A | 12/1980 | Stenson |
| 4,418,692 A | 12/1983 | Guay |
| 4,635,638 A | 1/1987 | Weintraub et al. |
| 4,890,615 A | 1/1990 | Caspari et al. |
| 5,015,250 A | 5/1991 | Foster |
| 5,053,043 A | 10/1991 | Gottesman et al. |

(Continued)

FOREIGN PATENT DOCUMENTS

DE    199 44 236    3/2001

(Continued)

OTHER PUBLICATIONS

International Search Report; PCT/US2008/064513 (Aug. 13, 2008).

(Continued)

*Primary Examiner*—Michael Peffley
*Assistant Examiner*—Samantha Good
(74) *Attorney, Agent, or Firm*—Brinks Hofer Gilson & Lione

(57) ABSTRACT

A medical device and method for performing transluminal procedures that reduces procedure time as well as the number of instruments used is disclosed. An elongate medical device has both a cutting tool and a suturing tool disposed at a distal end of the elongate medical device. The suturing tool includes a plurality of needles connected to one or more sutures. The elongate medical device is advanced through a bodily lumen to a position proximate the visceral wall. A perforation is formed in the visceral wall using the cutting tool. The elongate medical device and its suturing tool are advanced through the perforation and a plurality of needles are passed through the visceral wall around the periphery of the perforation. The plurality of needles are withdrawn through the bodily lumen and the perforation is closed using the suture.

16 Claims, 11 Drawing Sheets

U.S. PATENT DOCUMENTS

| | | | |
|---|---|---|---|
| 5,059,201 A | 10/1991 | Asnis | |
| 5,222,508 A | 6/1993 | Contarini | |
| 5,304,184 A | 4/1994 | Hathaway et al. | |
| 5,320,632 A | 6/1994 | Heidmueller | |
| 5,344,420 A | 9/1994 | Hilal et al. | |
| 5,350,385 A | 9/1994 | Christy | |
| 5,364,408 A | 11/1994 | Gordon | |
| 5,368,601 A | 11/1994 | Sauer et al. | |
| 5,374,275 A * | 12/1994 | Bradley et al. | 606/144 |
| 5,376,096 A | 12/1994 | Foster | |
| 5,380,321 A | 1/1995 | Yoon | |
| 5,389,103 A | 2/1995 | Melzer et al. | |
| 5,391,182 A | 2/1995 | Chin | |
| 5,403,329 A | 4/1995 | Hinchcliffe | |
| 5,405,354 A | 4/1995 | Sarrett | |
| 5,417,699 A | 5/1995 | Klein et al. | |
| 5,417,700 A * | 5/1995 | Egan | 606/144 |
| 5,439,469 A | 8/1995 | Heaven et al. | |
| 5,462,561 A * | 10/1995 | Voda | 606/144 |
| 5,470,338 A | 11/1995 | Whitfield et al. | |
| 5,476,469 A | 12/1995 | Hathaway et al. | |
| 5,478,353 A | 12/1995 | Yoon | |
| 5,562,683 A | 10/1996 | Chan | |
| 5,562,688 A | 10/1996 | Riza | |
| 5,571,090 A | 11/1996 | Sherts | |
| 5,571,119 A | 11/1996 | Atala | |
| 5,573,540 A | 11/1996 | Yoon | |
| 5,578,044 A | 11/1996 | Gordon et al. | |
| 5,586,986 A | 12/1996 | Hinchcliffe | |
| 5,599,347 A | 2/1997 | Hart et al. | |
| 5,643,292 A | 7/1997 | Hart | |
| 5,645,552 A | 7/1997 | Sherts | |
| 5,653,717 A | 8/1997 | Ko et al. | |
| 5,683,402 A | 11/1997 | Cosgrove et al. | |
| 5,700,273 A | 12/1997 | Buelna et al. | |
| 5,728,113 A | 3/1998 | Sherts | |
| 5,741,278 A | 4/1998 | Stevens | |
| 5,746,751 A | 5/1998 | Sherts | |
| 5,772,660 A | 6/1998 | Young et al. | |
| 5,792,153 A | 8/1998 | Swain et al. | |
| 5,824,010 A | 10/1998 | McDonald | |
| 5,836,955 A | 11/1998 | Buelna et al. | |
| 5,836,956 A | 11/1998 | Buelna et al. | |
| 5,846,253 A | 12/1998 | Buelna et al. | |
| 5,860,990 A | 1/1999 | Nobles et al. | |
| 5,865,836 A | 2/1999 | Miller | |
| 5,908,428 A | 6/1999 | Scirica et al. | |
| 5,931,844 A | 8/1999 | Thompson et al. | |
| 5,938,668 A | 8/1999 | Scirica et al. | |
| 5,984,919 A | 11/1999 | Hilal et al. | |
| 6,036,699 A * | 3/2000 | Andreas et al. | 606/139 |
| 6,248,124 B1 * | 6/2001 | Pedros et al. | 606/213 |
| 6,348,059 B1 | 2/2002 | Hathaway et al. | |
| 6,355,050 B1 | 3/2002 | Andreas et al. | |
| 6,719,763 B2 | 4/2004 | Chung et al. | |
| 6,755,843 B2 | 6/2004 | Chung et al. | |
| 6,955,643 B2 | 10/2005 | Gellman et al. | |
| 6,972,027 B2 | 12/2005 | Fallin et al. | |
| 6,988,987 B2 | 1/2006 | Ishikawa | |
| 6,997,931 B2 | 2/2006 | Sauer et al. | |
| 7,060,078 B2 | 6/2006 | Hathaway et al. | |
| 7,081,124 B2 | 7/2006 | Sancoff et al. | |
| 7,112,207 B2 | 9/2006 | Allen et al. | |
| 7,118,583 B2 | 10/2006 | O'Quinn et al. | |
| 7,122,039 B2 | 10/2006 | Chu | |
| 7,122,040 B2 | 10/2006 | Hill et al. | |
| 7,144,401 B2 | 12/2006 | Yamamoto et al. | |
| 7,157,636 B2 | 1/2007 | Hsieh | |
| 7,166,116 B2 | 1/2007 | Lizardi et al. | |
| 7,175,636 B2 | 2/2007 | Yamamoto et al. | |
| 7,232,448 B2 | 6/2007 | Battles et al. | |
| 7,273,451 B2 | 9/2007 | Sekine et al. | |
| 7,323,004 B2 | 1/2008 | Parahar | |
| 7,326,221 B2 | 2/2008 | Sakamoto | |
| 7,344,545 B2 | 3/2008 | Takemoto et al. | |
| 7,399,304 B2 * | 7/2008 | Gambale et al. | 606/139 |
| 7,407,505 B2 | 8/2008 | Sauer et al. | |
| 7,527,590 B2 | 5/2009 | Suzuki et al. | |
| 7,530,985 B2 | 5/2009 | Takemoto et al. | |
| 7,708,748 B2 | 5/2010 | Weisenburgh, II et al. | |
| 2002/0116010 A1 | 8/2002 | Chung et al. | |
| 2002/0116011 A1 | 8/2002 | Chee Chung et al. | |
| 2002/0198542 A1 | 12/2002 | Yamamoto et al. | |
| 2003/0045891 A1 | 3/2003 | Yamamoto et al. | |
| 2003/0181924 A1 | 9/2003 | Yamamoto et al. | |
| 2003/0216613 A1 | 11/2003 | Suzuki et al. | |
| 2004/0092965 A1 * | 5/2004 | Parihar | 606/144 |
| 2004/0147941 A1 | 7/2004 | Takemoto et al. | |
| 2005/0143762 A1 | 6/2005 | Paraschac et al. | |
| 2005/0149067 A1 | 7/2005 | Takemoto et al. | |
| 2005/0251165 A1 | 11/2005 | Vaughan et al. | |
| 2005/0251166 A1 | 11/2005 | Vaughan et al. | |
| 2006/0020274 A1 | 1/2006 | Ewers et al. | |
| 2006/0190016 A1 | 8/2006 | Onuki et al. | |
| 2006/0253144 A1 | 11/2006 | Mikkaichi et al. | |
| 2006/0271101 A1 | 11/2006 | Saadat et al. | |
| 2006/0282089 A1 | 12/2006 | Stokes et al. | |
| 2007/0093858 A1 | 4/2007 | Gambale et al. | |
| 2007/0100375 A1 | 5/2007 | Mikkaichi et al. | |
| 2007/0100376 A1 | 5/2007 | Mikkaichi et al. | |
| 2007/0112362 A1 | 5/2007 | Mikkaichi et al. | |
| 2007/0123840 A1 | 5/2007 | Cox | |
| 2007/0191886 A1 | 8/2007 | Dejima et al. | |
| 2007/0197864 A1 | 8/2007 | Dejima et al. | |
| 2007/0198000 A1 | 8/2007 | Miyamoto et al. | |
| 2007/0213702 A1 | 9/2007 | Kogosaka et al. | |
| 2007/0255296 A1 | 11/2007 | Sauer | |
| 2007/0260121 A1 | 11/2007 | Bakos et al. | |
| 2007/0276424 A1 | 11/2007 | Mikkaichi et al. | |
| 2008/0114379 A1 | 5/2008 | Takemoto et al. | |
| 2008/0114380 A1 | 5/2008 | Takemoto et al. | |
| 2008/0185752 A1 | 8/2008 | Cerwin et al. | |
| 2008/0243148 A1 | 10/2008 | Mikkaichi et al. | |
| 2008/0262525 A1 | 10/2008 | Chang et al. | |
| 2009/0076527 A1 | 3/2009 | Miyamoto et al. | |
| 2009/0125039 A1 | 5/2009 | Mikkaichi et al. | |

FOREIGN PATENT DOCUMENTS

| | | |
|---|---|---|
| WO | WO 93/01750 | 2/1993 |
| WO | WO 01/01868 | 1/2001 |
| WO | WO 2004/103157 | 12/2004 |
| WO | WO 2008/045376 | 4/2008 |

OTHER PUBLICATIONS

International Search Report; PCT/US2008/073082 (Nov. 21, 2008).
International Search Report; PCT/US2009/030030 (Aug. 19, 2009).

\* cited by examiner

DEVICE TO OPEN AND CLOSE A BODILY WALL

CROSS-REFERENCE TO RELATED APPLICATIONS

This application claims the benefit of U.S. Provisional Application Ser. No. 60/956,569, filed on Aug. 17, 2007, entitled "DEVICE TO OPEN AND CLOSE A BODILY WALL"

FIELD OF THE INVENTION

The present invention relates generally to medical devices for cutting open and suturing closed the visceral walls of bodily lumens.

BACKGROUND OF THE INVENTION

Perforations in visceral walls may be formed to gain access to adjacent structures of the body, the methods commonly referred to as transluminal procedures. For example, culdoscopy was developed over 70 years ago, and involves transvaginally accessing the peritoneal cavity by forming a perforation in the cul de sac. This access to the peritoneal cavity allows medical professionals to visually inspect numerous anatomical structures, as well as perform various procedures such as biopsies or other operations. Many transluminal procedures for gaining access to different body cavities using other bodily lumens are also being developed.

Generally, transluminal procedures require the use of several different medical instruments, and therefore can be time consuming. At a minimum, a cutting instrument is first used to form the perforation, an endoscope or other visualizing device is used to inspect the area or otherwise perform some procedure, and then one or more closure instruments are used to close the perforation. There is also the risk of perforating structures that lie just beyond the bodily wall being cut. For example, when incising the gastric wall, the potential of hitting blood vessels without knowing could lead to bleeding complications. Accidentally puncturing the small intestines could lead to the spillage of bacteria into the peritoneal cavity. Depending on the structure being cut, it has also proven difficult to adequately close the perforation and prevent leakage of bodily fluids to reduce the risk of infection. For example, anastomotic leaks are seen in up to 10% of laparoscopic gastrojejunostomies.

BRIEF SUMMARY OF THE INVENTION

The present invention provides medical devices and methods for performing transluminal procedures that reduce procedure time as well as the number of instruments used. At about the same time, the medical device and method safely form a perforation and prepare the perforation for reliable closure. One embodiment of a method for opening and closing a visceral wall employs an elongate medical device having both a cutting tool and a suturing tool disposed at a distal end of the elongate medical device. The suturing tool includes a plurality of needles connected to one or more sutures. The elongate medical device is advanced through a bodily lumen to a position proximate the visceral wall. A perforation is formed in the visceral wall using the cutting tool. The elongate medical device and its suturing tool are advanced through the perforation. The plurality of needles are passed through the visceral wall around the periphery of the perforation by retracting the elongate medical device and its suturing tool. The plurality of needles are withdrawn through the bodily lumen and ultimately the perforation is closed using the suture.

According to more detailed aspects of this embodiment, the method further includes passing medical instrumentation through the perforation and performing a medical procedure with the medical instrumentation after the plurality of needles have been passed through the visceral wall. The plurality of needles are moved radially outwardly prior to retracting the elongate medical device to pass the plurality of needles through the visceral wall. A grasping device may be advanced through the bodily lumen to grasp at least one of the plurality of needles, and is then retracted. An overtube may also be advanced to the bodily lumen, the overtube including a plurality of accessory channels that can be aligned with the plurality of needles to withdraw the needles therethrough. The elongate medical device preferably has a lumen extending through the cutting tool and through the suturing tool at the distal end. The method can include advancing an instrument through the lumen such as a visualization instrument which can be used to visualize the visceral wall prior to the step of forming the perforation.

According to another embodiment, an elongate medical device is provided for opening and closing a visceral wall. The medical device generally comprises an outer catheter defining a first lumen and an inner cannula defining a second lumen. The inner cannula is slideably disposed within the first lumen and has a distal end extending beyond a distal end of the outer catheter. The elongate medical device also includes a needle deployment linkage attached to the outer catheter and to the inner cannula. The needle deployment linkage is operable between a delivery configuration and a deployed configuration for placing a plurality of needles through the visceral wall. The cutting tool is attached to the distal end of the inner cannula and defines a third lumen in communication with the second lumen of the inner cannula.

According to more detailed aspects of this embodiment, a protective tip is slideably disposed within the third lumen of the cutting tool. The protective tip is spring biased to project from a distal end of the cutting tool. The protective tip defines an access channel therethrough, the access channel being in communication with the second lumen. Preferably, the cutting tool is an electro-surgical cutting tool. Most preferably, the protective tip has a first contact attached thereto and the inner cannula has a second contact attached thereto. The first and second contacts form a switch which opens and closes to deenergize and energize the electrosurgical cutting tool.

Yet another embodiment provides an elongate medical device for opening and closing a visceral wall. The medical device generally comprises an outer catheter, an inner cannula, a cutting tool, and a needle deployment linkage. The outer catheter defines a first lumen and the inner cannula defines a second lumen. The inner cannula is slideably disposed within the first lumen and has a distal end extending beyond a distal end of the outer catheter. The cutting tool is attached to the distal end of the inner cannula. The needle deployment linkage is attached to the distal end of the outer catheter and attached to the inner cannula at a position generally proximal the cutting tool. The needle deployment linkage is operable between a delivery configuration and a deployed configuration. Relative translation of the outer catheter and inner cannula operates the needle deployment linkage between the delivery configuration and the deployed configuration. A plurality of needles are attached to the needle deployment linkage, the plurality of needles being connected to one or more sutures.

According to more detailed aspects, the plurality of needles move radially outwardly between the delivery configuration and deployed configuration. The needle deployment linkage includes a plurality of linkage sets, each linkage set having a first link pivotally connected to the outer catheter and a second link pivotally connected to the inner cannula. The first and second links rotate radially outwardly as the needle deployment linkage moves between the delivery and deployed configurations. Preferably, each linkage set further comprises a third link interconnecting the first and second links, the third link pivotally connected to both the first and second links. The plurality of needles are connected to the third link of the plurality of linkage sets. Each third link defines a pocket size to receive a needle, each pocket opening proximally. Each pocket also includes a radially opening slot sized to receive the suture attached to the needle.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
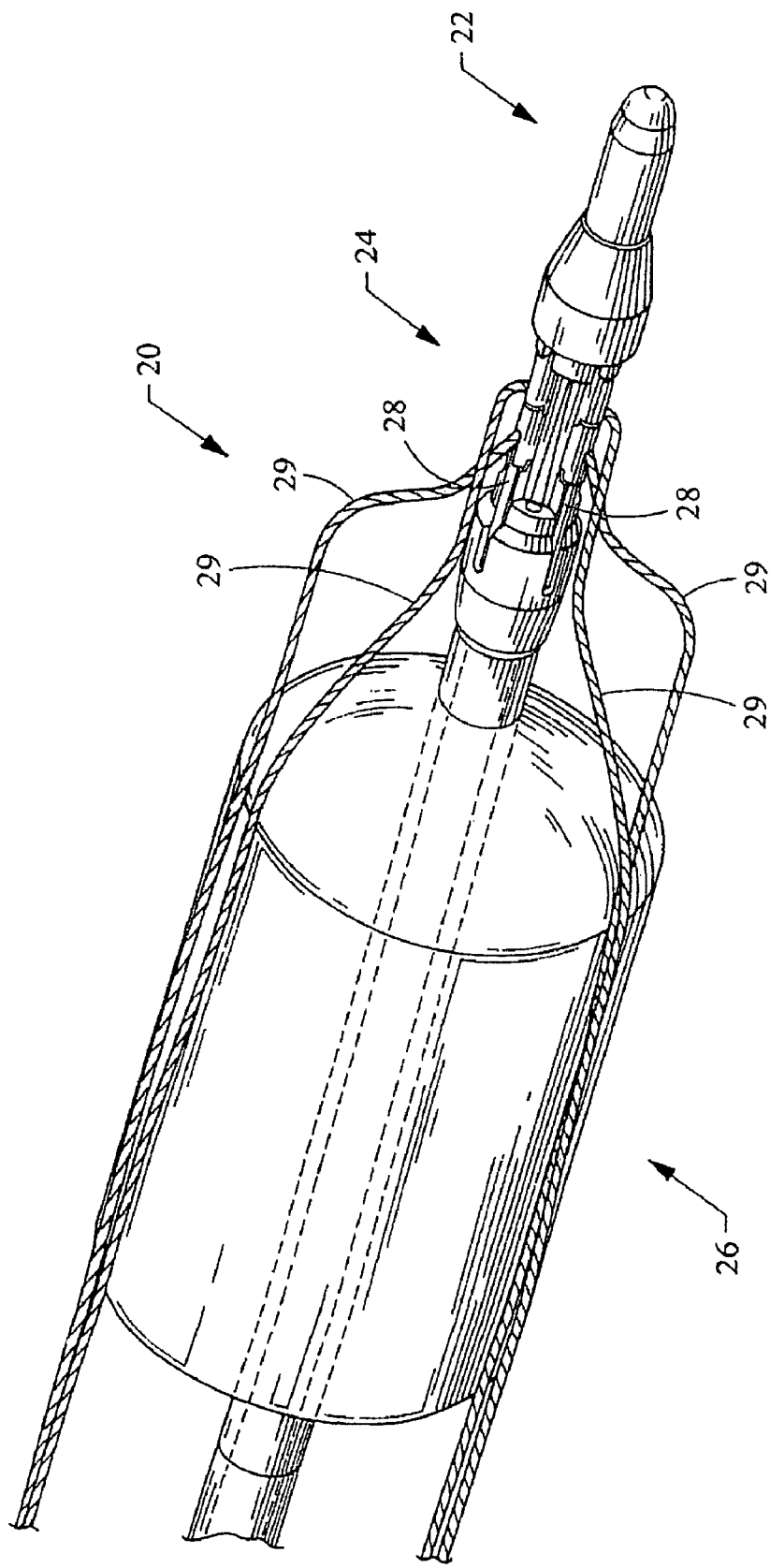
FIG. 1 is a perspective view of an elongate medical device constructed in accordance with the teachings of the present invention.
Figure 2:
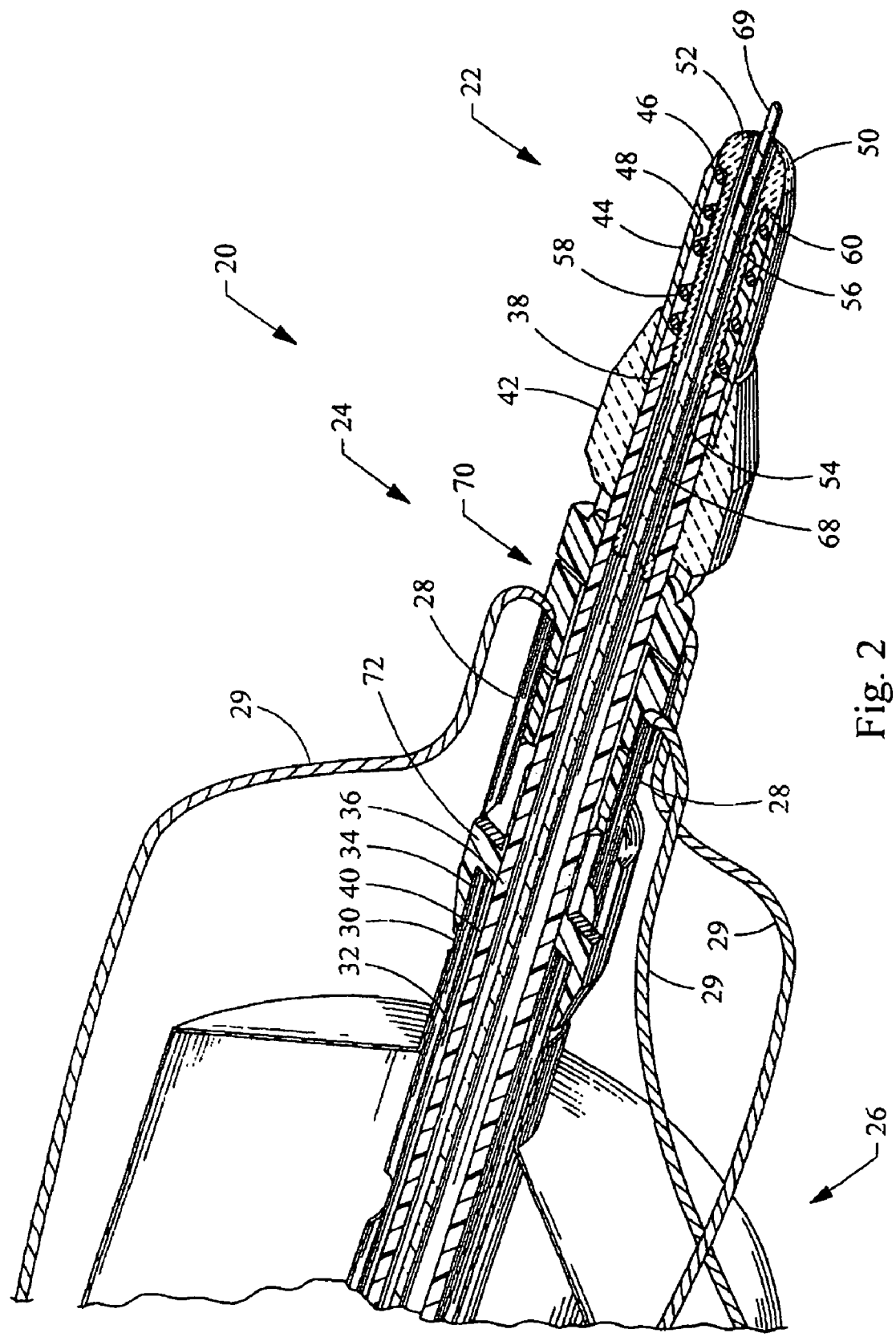
FIG. 2 is an enlarged isometric cross-section of the elongate medical device depicted in FIG. 1.
Figure 3:
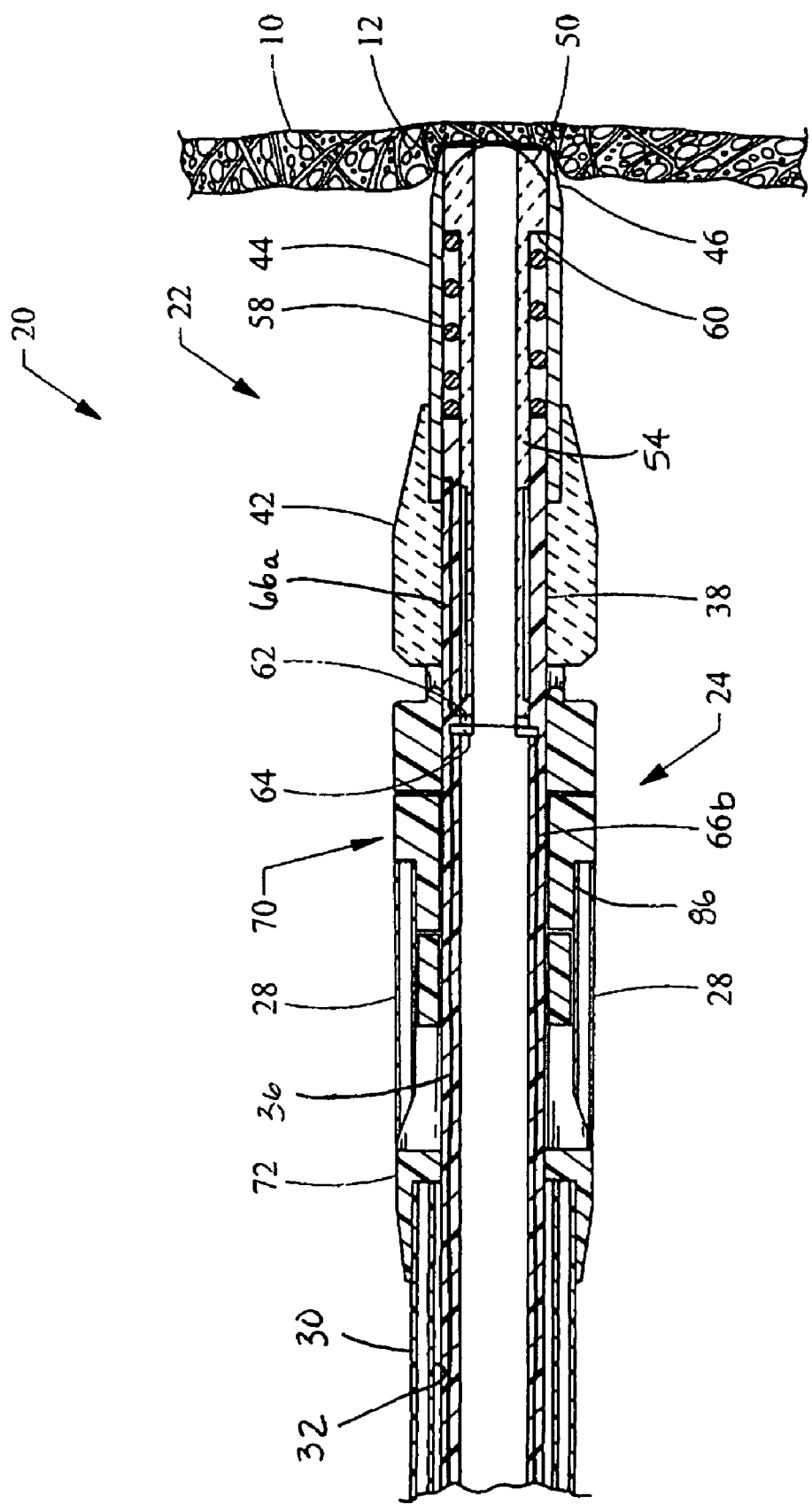
FIG. 3 is cross-sectional view of the elongate medical device depicted in FIG. 1.

Turning now to the figures, an elongate medical device 20 for non-invasively opening and closing a visceral wall has been depicted in FIGS. 1-5, and is constructed in accordance with the teachings of the present invention. The medical device 20 generally includes a cutting tool 22, a suturing tool 24, and a dilation tool 26. The cutting tool 22 is used to form a perforation 12 in a visceral wall 10 (FIG. 3). The suturing tool 24 is used to place a plurality of needles 28 through the visceral wall 10, the needles 28 being connected to one or more sutures 29 for closing the perforation 12. The dilation tool 26 is used to dilate the perforation 12.

As shown in FIG. 2, the elongate medical device 20 is generally defined by a double-walled outer catheter 30 defining a first lumen 32, and an inner cannula 36 defining a second lumen 40. The inner cannula 36 projects beyond a distal end 34 of the outer catheter 30. The distal end 38 of the inner cannula 36 is connected to the cutting tool 22. The suturing tool 24 is generally connected to the distal end 34 of the outer catheter 30, as well as to the inner cannula 36 by way of a hub 42.

The cutting tool 22 generally comprises an electrosurgical needle-knife 44 which is connected to, and projects distally from, the distal end 38 of the inner cannula 36. The hub 42 is preferably made of a non-conductive material such as ceramic, and is used to connect the needle-knife 44 to the inner cannula 36. The needle-knife 44 defines a third lumen 48 which is in communication with the second lumen 40. The needle-knife 44 includes a sharpened distal tip 46 for piercing tissue while a needle knife 44 has been depicted as the cutting tool 22, other monopolar or bipolar electrosurgical tools may be employed, or non-electrical cutting tools.

The cutting tool 22 also includes a protective tip 50 having an atraumatic distal end 52 which is shown as a semi-spherical member in the figures. An elongated body 54 of the protective tip 50 projects proximately into the second lumen 40 of the inner cannula 36. The protective tip 50 defines an access channel 56 extending therethrough which is in communication with the second lumen 40. As such, a fiber optic imaging device 68 may be utilized in conjunction with the medical tool 20 of the present invention, as will be described in further detail hereinbelow. The protective tip 50 is spring biased to project from the distal end 46 of the needle-knife 44. As shown, a spring 58 abuts against the distal end 38 of the inner cannula 36, and also rests against a shoulder 60 formed by the distal end 52 and body 54 of the protective tip 50. When the medical device 20 is pressed against tissue 10, the force of spring 58 will be overcome and the protective tip 50 will move proximally within the third lumen 48 defined by the needle-knife 44. As such, the protective tip 50 is operable between an extended position projecting from the distal end 46 of the needle knife 44 (as shown in FIG. 2) and a retracted position located within the third lumen 48 (as shown in FIG. 3).

As best seen in FIG. 3, the spring biased protective tip 50 also serves to form a switch for selectively energizing and deenergizing the needle-knife 44. Generally, a first contact 62 is formed at a proximal end of the body 54 of the protective tip 50, while a second contact 64 is fixed to the inner cannula 36. A first wire 66a connects the needle-knife 44 to the first contact 62, while a second wire 66b connects the second contact 64 to a power supply. In operation, when the cutting tool 22 is pressed against tissue 10, the protective tip 50 is biased to its retracted position, whereby the first and second contacts 62, 64 will engage to close the switch and electrically connect the wires 66a, 66b, and thereby energize the needle-knife 44. Upon forming a complete perforation 12 in the tissue 10, the protective tip 50 will be biased to its extended position by the spring 58, whereby the switch opens via the disconnection of first and second contacts 62, 64. It will be recognized by those skilled in the art that other types of electrosurgical tools may be used as the cutting tool 22, with or without a protective tip 50, and with or without a switch. It will also be recognized that an override switch may also be provided to allow energization of the needle-knife 44 despite the disconnection of the first and second contacts 62, 64 (i.e., the extended position of the protective tip 50). For example, a wire leading direct from either the second wire 66b or second contact 64 may be connected to a manually operated switch located on the proximal end of the medical device 20. This may be particularly useful when the annular side surface of the needle-knife 44 is desired to be used for cutting, such as for enlarging the perforation 12 after it is initially formed.

Referring to FIG. 2, a fiber optic imaging device 68 such as an imaging catheter is preferably utilized to visually inspect the bodily wall 10 and select the site for forming perforation 12. As such, the fiber optic imaging device 68 is passed through the second lumen 40 of the inner cannula 36, as well as through the accessory channel 56 of the protective tip 50, such that the distal end 69 of the imaging device 68 projects beyond the distal-most tip of the cutting tool 22 and medical device 20. The imaging device 68 is then withdrawn to permit normal operation of the needle-knife and protective tip 50.

Details of the suturing tool 24 and its operation will now be described with reference to FIGS. 4 and 5. The suturing tool 24 generally comprises a needle deployment linkage 70 which includes a plurality of linkage sets 70a, 70b, 70c, 70d corresponding to the plurality of needles 28. The needle deployment linkage 70 is connected to the outer catheter 30 by way of support hub 72 (see also FIG. 2). The support hub 72 includes a plurality of recesses 74 which are sized to receive the sharp ends of the needles 28 and provide protection therefor. The needle deployment linkage 70 is also connected to the base 42, which in turn is connected to the inner cannula 36 (see FIG. 2). Each linkage set 70a, 70b, 70c, 70d of the deployment linkage 70 includes a first link 80, a second link 82 and a third link 84. The first link 80 is pivotally connected to the hub 72 while the second link 82 is pivotally connected to the base 42. The third link 84 is pivotally connected to both the first and second links 80, 82, and is structured for retaining a needle 28. Each third link 84 includes a pocket 86 having a slot 88. The pocket 86 is sized to receive the base end of a needle 28, while the slot 88 is sized to permit passage of the suture 29 therethrough.

Figure 4:
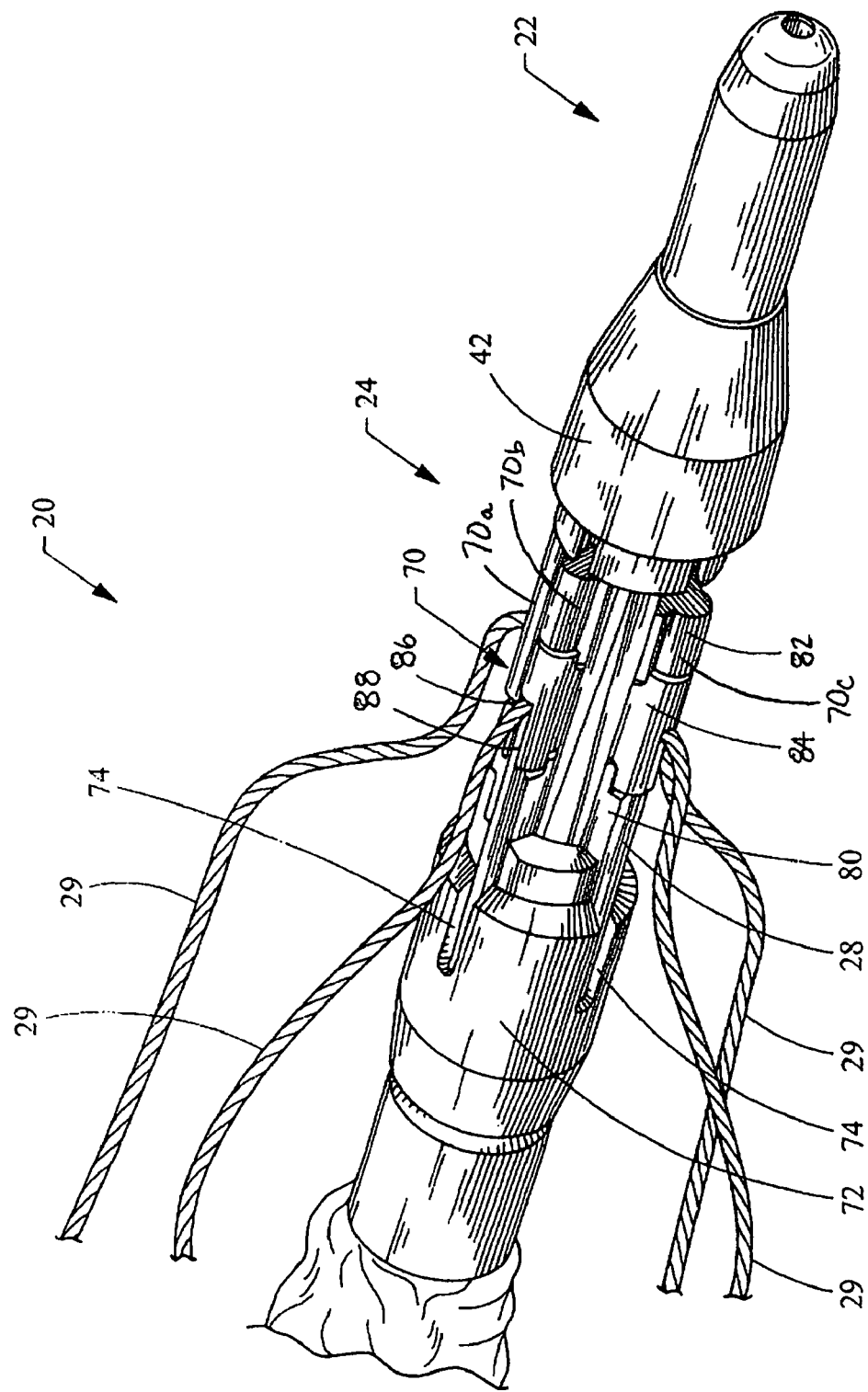
FIG. 4 is an enlarged perspective view of the elongate medical device depicted in FIG. 1, showing a delivery configuration.
Figure 5:
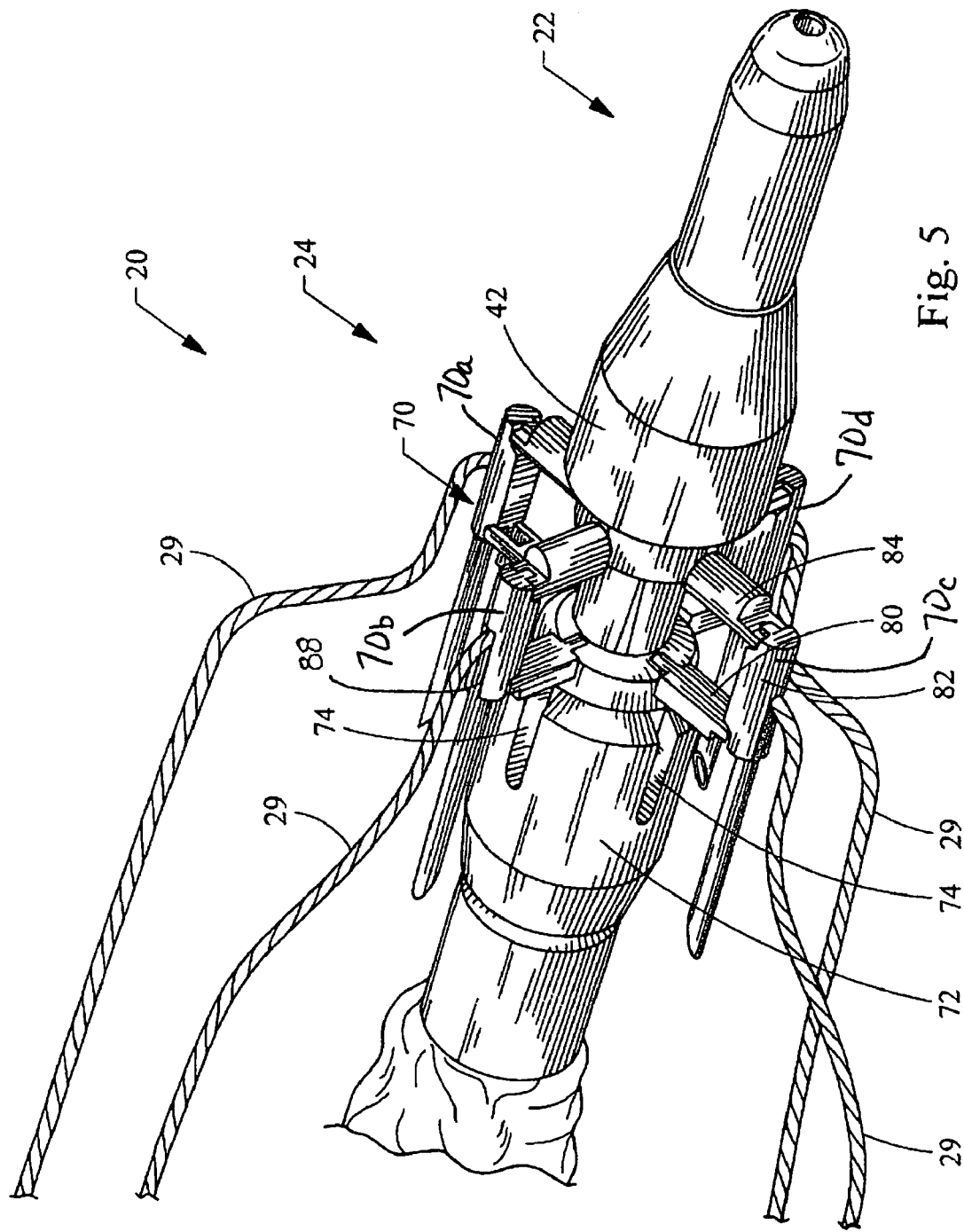
FIG. 5 is an enlarged perspective view of the elongate medical device depicted in FIG. 1, showing the deployment configuration.

The needle deployment linkage 70 is operable between a delivery configuration as shown in FIG. 4, and a deployed configuration as shown in FIG. 5. Through relative translation of the inner cannula 36 and outer catheter 30, and in particular by bringing their distal ends 34, 38 closer together, the first, second and third links 80, 82, 84 are forced to pivot relative to one another and relative to the base and hub 42, 72. In particular, the first and second links 80, 82 are rotated radially outwardly and the third link 84 is moved radially away from a longitudinal axis of the medical device 20. Notably, the third link 84 remains generally parallel to the cannula 36, as do the needles 28. The pockets 86 generally opens proximally while the slots 88 open radially. In this deployed configuration, the third links 84 and needles 28 are positioned for placement through the visceral wall 10 around the perforation 10. The proximally opening pockets 86 readily support needle placement, while also permitting easy release of the needles 28 and the suture 29 once placed.

Figure 6:
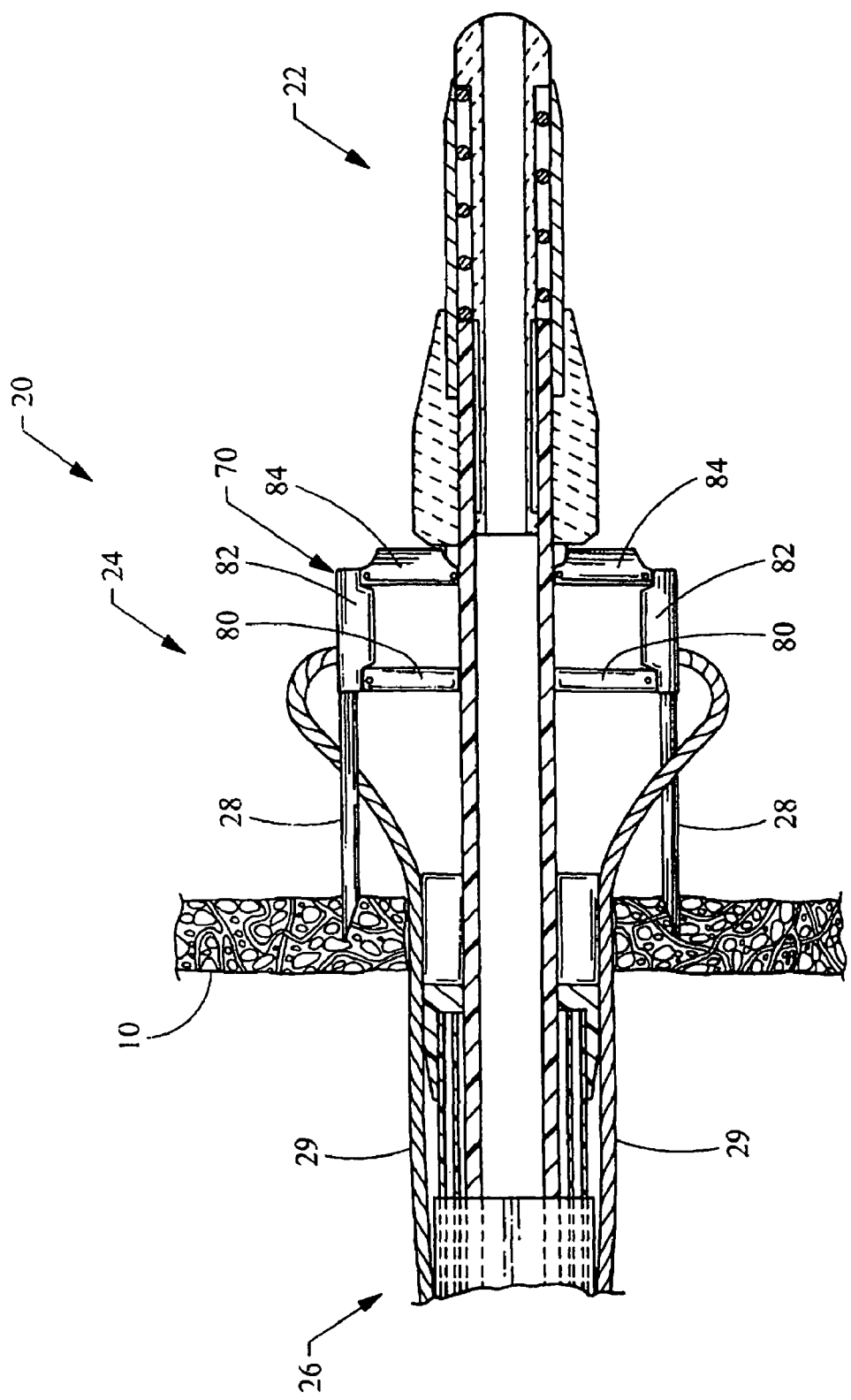
FIGS. 6-11 are cross-sectional and isometric views depicting a method for employing the elongate medical device depicted in FIG. 1.

Having described the medical device 20, one method for its use will now be described with reference to FIGS. 3 and 6-11. Generally, the medical device 20 is advanced through a bodily lumen such as the alimentary canal (not shown) to a position proximate a visceral wall 10 such as the stomach wall. The imaging device 68 may be used to visually inspect and select a portal site in the wall 10. The cutting tool 22 is pressed against the wall 10 to retract the protective tip 50, and is manipulated to form a perforation 12 in the visceral wall 10. The override switch may be used as necessary. As shown in FIG. 6, the medical device and its suturing tool 24 are advanced through the perforation 12. The needle deployment linkage 70 of the suturing tool 24 is operated into its deployment configuration such that the needles 28 are exposed and positioned radially outwardly from the inner cannula 36 and outer catheter 30 of the medical device 20. The medical device 20 is then retracted in order to pass the plurality of needles 28 through the visceral wall 10 at locations around the periphery of the perforation 12.

Figure 7:
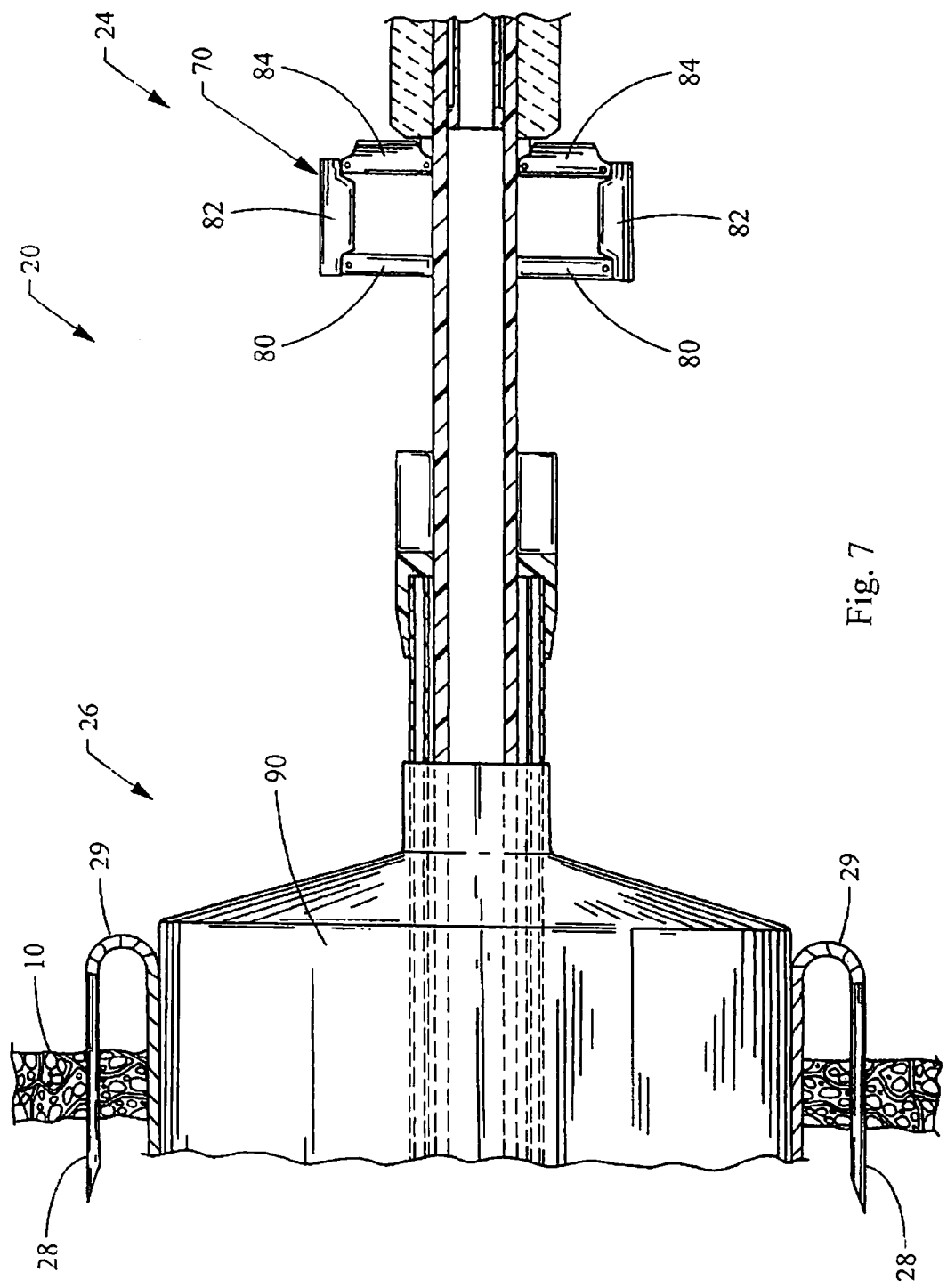

As shown in FIG. 7, the medical device 20 is again advanced in order to detach the needles 28 from the deployment linkage 70, and leave the needles 28 placed through the visceral wall 20. At about the same time, the dilation balloon 90 of the dilation device 26 is inflated by introducing a fluid such as air or saline through the double-wall outer catheter 30 (i.e., through a supply channel fluidically connected to the balloon 90) thereby dilating the perforation 12 formed in the visceral wall 10.

At this point in the procedure, other medical instruments may be passed through the medical device 20 and beyond the distal end of the cutting tool's protective tip 50, such as the fiber optic imaging device 68 depicted in FIG. 2. For example, the peritoneal cavity could be explored and visually inspected for certain conditions. Likewise, numerous types of medical tools may be employed for performing various operations such as biopsy tools, cutting tools, grasping devices and the like. It will also be recognized that the medical device 20 may be completely withdrawn through the bodily lumen so that an endoscope or other larger medical instrumentation may be employed through the enlarged perforation 12.

Figure 8:
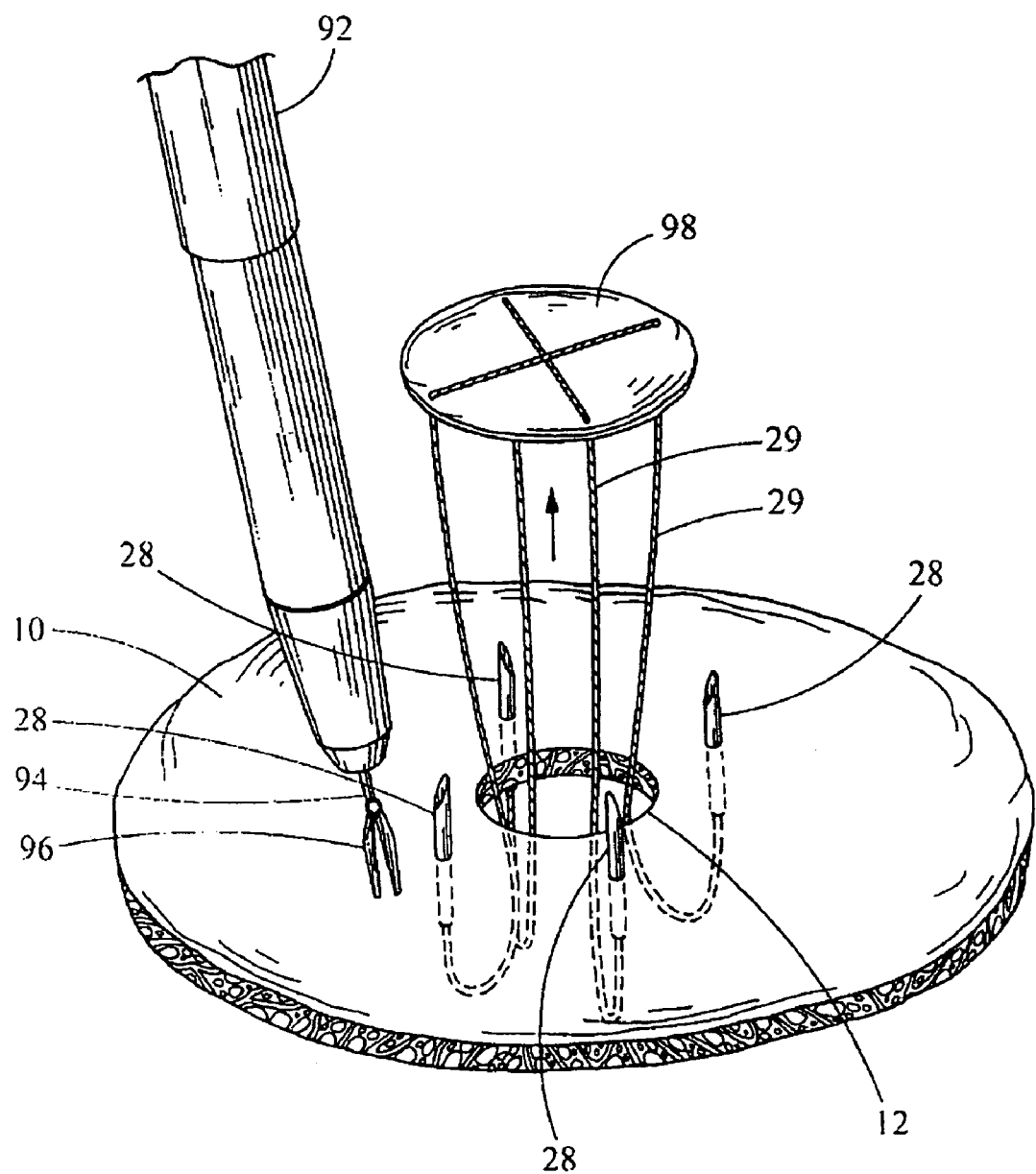

To close the perforation 12, the suture 29 connected to the needles 28 is preferably linked to a tissue patch 98 as shown in FIG. 8. The tissue patch 98 is preferably small intestinal submucosa (SIS), such as SURGISIS® BIODESIGN™ Soft Tissue Graft, available from Cook Biotech, Inc., West Lafayette, Ind., which provides smart tissue remodeling through its three-dimensional extracellular matrix (ECM) that is colonized by host tissue cells and blood vessels, and provides a scaffold for connective and epithelial tissue growth and differentiation along with the ECM components. Preferably, the intestinal patch would be a one to four layer lyophilized soft tissue graft made from any number of tissue engineered products. Reconstituted or naturally-derived collagenous materials can be used, and such materials that are at least bioresorbable will provide advantage in the present invention, with materials that are bioremodelable and promote cellular invasion and ingrowth providing particular advantage. Suitable bioremodelable materials can be provided by collagenous ECMs possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. The patch may also be a composite of a biomaterial and a biodegradable polymer. Additional details may be found in U.S. Pat. No. 6,206,931 to Cook et al., the disclosure of which is incorporated herein by reference in its entirety.

Figure 9:
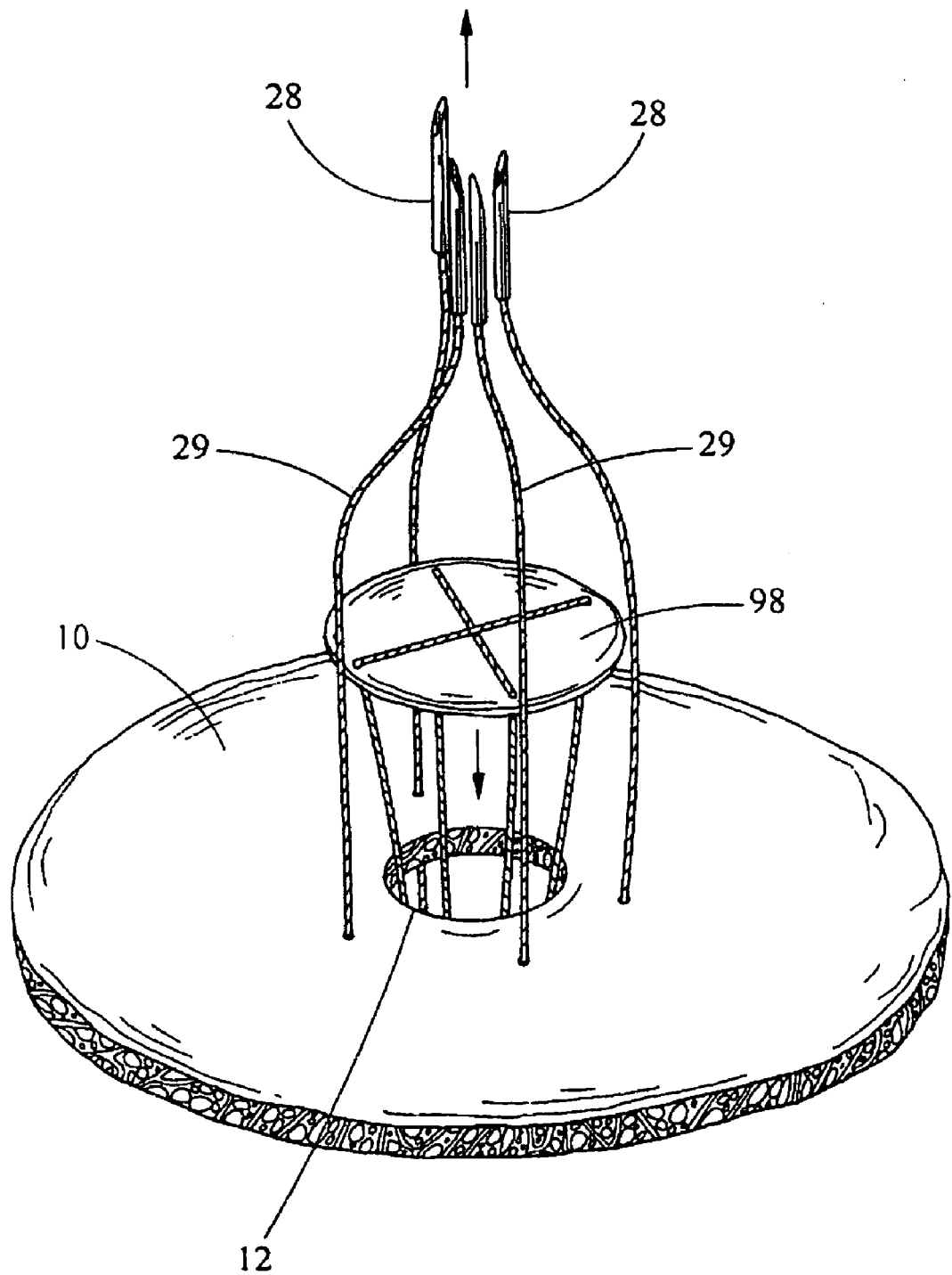
Figure 10:
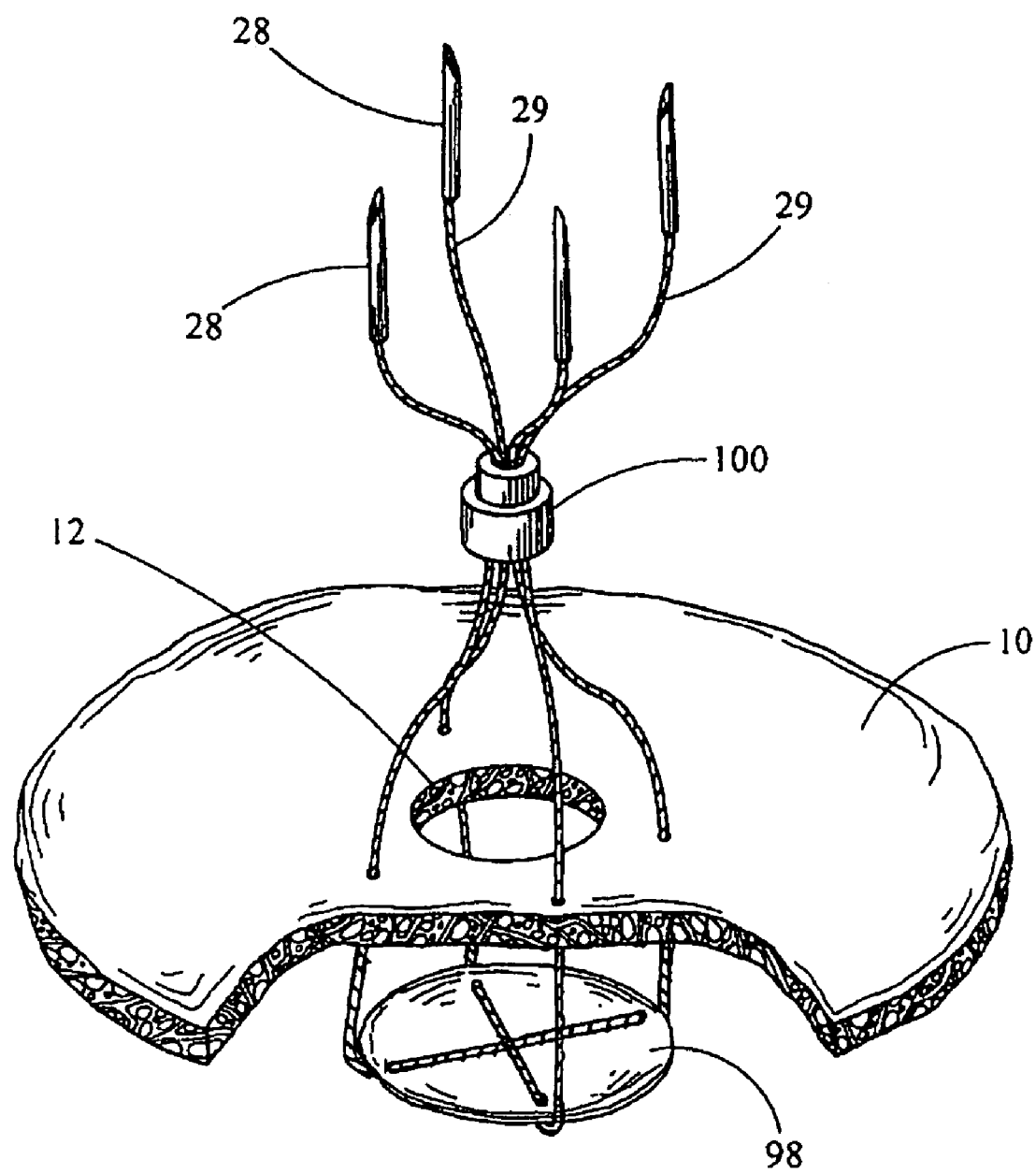
Figure 11:
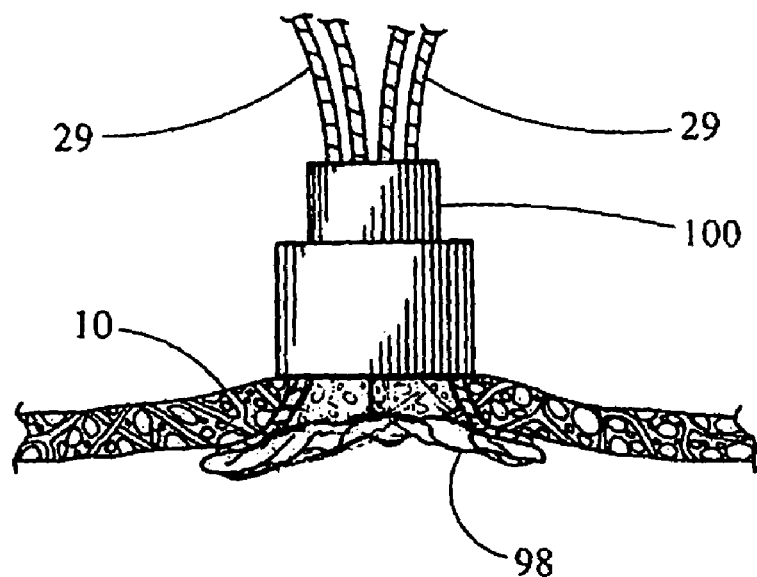

The plurality of needles 28 are grasped and retracted through the bodily lumen, preferably by way of an endoscope 92 having a retrieval tool 94 such as grasping forceps 96 for collecting the needles 28 and pulling them fully through the visceral wall 10. As shown in FIG. 9, the needles 28 are further retracted, thereby pulling the tissue patch 98 through the perforation 12 to the distal side of the visceral wall 10. As shown in FIG. 10, a suture collet 100 is utilized to tension the suture 29 and draw the perforation 12 closed with the assistance of tissue patch 98, as shown in FIG. 11. It will be recognized by those skilled in the art that the tissue patch 98, while preferred, need not be employed to fully close the perforation 12.

Figure 12:
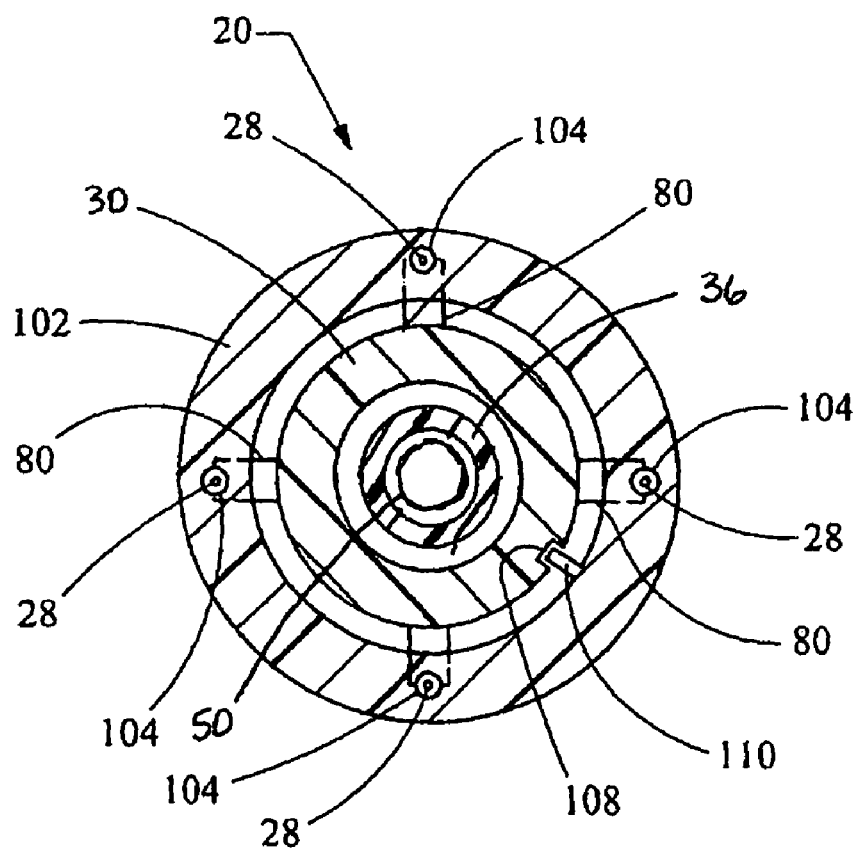
FIG. 12 is a cross-sectional view of the elongate medical device depicted in FIG. 1, showing its use with an overtube.

Referring to FIG. 12, another optional feature, an overtube 102, may be used to deliver the elongate medical device 20 through the bodily lumen into the visceral wall 10. Preferably, the overtube 102 is also specially adapted for retrieving the plurality of needles 28 after the needles 28 have been deployed by way of the deployment linkage 70. As shown, the overtube 102 includes a plurality of retrieval channels 104 extending longitudinally therethrough. The channels 104 are circumferentially spaced to correspond to the linkage sets 70a, 70b, 70c, 70d in the needle deployment linkage. Preferably, the relative position of the channels 104 and deployment linkage 70 may be maintained through use of a notch 108 formed in the inner surface of the overtube 102 and a mating projection 110 formed on the outer surface of the outer catheter 30. Numerous other types of mating features may be used to positively position the overtube 102 relative to the elongate medical device 20, or no mating feature at all. In either case, grasping forceps or the like may be introduced through the retrieval channels 104 in the overtube 102 to grasp the needles 28 after they have been placed through the visceral wall 10 (grasp and retrieve).

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An elongate medical device for opening and closing a visceral wall, the medical device comprising:
   an outer catheter defining a first lumen;
   an inner cannula defining a second lumen, the inner cannula slidably disposed within the first lumen, the inner cannula having a distal end extending beyond a distal end of the outer catheter;
   a needle deployment linkage having a plurality of needles connected to one or more sutures, the needle deployment linkage attached to the outer catheter and to the inner cannula, the needle deployment linkage operable between a delivery configuration and a deployed configuration for placing the needles through the visceral wall; and
   a cutting tool attached to the distal end of the inner cannula, the cutting tool defining a third lumen in communication with the second lumen of the inner cannula.

2. The elongate medical device of claim 1, further comprising a protective tip slidably disposed within the third lumen of the cutting tool, the protective tip being spring biased to project from a distal end of the cutting tool.

3. The elongate medical device of claim 2, wherein the protective tip is operable between an extended position projecting from the distal end of the cutting tool and a retracted position within the third lumen.

4. The elongate medical device of claim 3, wherein the cutting tool is an electrosurgical cutting tool, and wherein the protective tip has a first contact attached thereto, and wherein the inner cannula has a second contact attached thereto, the first and second contacts forming a switch, the switch opening and closing to deenergize and energize the electrosurgical cutting tool.

5. The elongate medical device of claim 4, wherein retracted position of the protective tip closes the switch to energize the electrosurgical cutting tool, and wherein the extended position of the protective tip opens the switch to deenergize the electrosurgical cutting tool.

6. The elongate medical device of claim 1, wherein the needle deployment linkage is attached to inner cannula at a position generally proximal to the cutting tool.

7. An elongate medical device for opening and closing a visceral wall, the medical device comprising:
   an outer catheter defining a first lumen;
   an inner cannula defining a second lumen, the inner cannula slidably disposed within the first lumen, the inner cannula having a distal end extending beyond a distal end of the outer catheter;
   a cutting tool attached to the distal end of the inner cannula; and
   a needle deployment linkage attached to the distal end of the outer catheter and attached to the inner cannula at a position generally proximal to the cutting tool, the needle deployment linkage operable between a delivery configuration and a deployed configuration, relative translation of the outer catheter and inner cannula operating the needle deployment linkage between the delivery configuration and the deployed configuration; and
   a plurality of needles attached to the needle deployment linkage, the plurality of needles connected to one or more sutures.

8. The elongate medical device of claim 7, wherein the plurality of needles move radially outwardly between the delivery and deployed configurations.

9. The elongate medical device of claim 7, wherein the needle deployment linkage includes a plurality of linkage sets, each linkage set having a first link pivotally connected to the outer catheter and a second link pivotally connected to the inner cannula, and wherein the first and second links rotate radially outwardly as the needle deployment linkage moves between the delivery and deployed configurations.

10. The elongate medical device of claim 9, wherein each linkage set further comprises a third link interconnecting the first and second links, the third link pivotally connected to both the first and second links.

11. The elongate medical device of claim 10, wherein the plurality of needles are connected to the third link of the plurality of linkage sets.

12. The elongate medical device of claim 11, wherein each third link defines a pocket sized to receive a needle, each pocket opening proximally and including a radially opening slot sized to receive the suture attached to the needle.

13. The elongate medical device of claim 7, further comprising a hub attached to the distal end of the outer catheter, the hub having a plurality of recesses sized and positioned to receive a portion of the plurality of needles in the delivery configuration.

14. The elongate medical device of claim 7, further comprising a base connected to the inner cannula, and wherein the cutting tool is attached to the base, and wherein the second link is pivotally attached to the base.

15. The elongate medical device of claim 7, further comprising an overtube having a lumen sized to receive the outer catheter.

16. The elongate medical device of claim 15, wherein the overtube includes a plurality of accessory channels, each accessory channel sized to receive a needle therein.

* * * * *